(12) United States Patent
Olivier et al.

(10) Patent No.: US 8,281,661 B2
(45) Date of Patent: Oct. 9, 2012

(54) ULTRASONIC ACOUSTIC EMISSIONS TO DETECT SUBSTRATE FRACTURE

(75) Inventors: Keith G. Olivier, Jackson, MI (US); Thomas Custer, Brighton, MI (US)

(73) Assignee: Tenneco Automotive Operating Company Inc., Lake Forest, IL (US)

( * ) Notice: Subject to any disclaimer, the term of this patent is extended or adjusted under 35 U.S.C. 154(b) by 320 days.

(21) Appl. No.: 12/788,882

(22) Filed: May 27, 2010

(65) Prior Publication Data
US 2011/0290025 A1   Dec. 1, 2011

(51) Int. Cl.
*G01N 29/14* (2006.01)
(52) U.S. Cl. .................. 73/587; 73/602; 73/627
(58) Field of Classification Search ......... 73/587, 73/588, 627, 788, 801, 804, 602
See application file for complete search history.

(56) References Cited

U.S. PATENT DOCUMENTS

| | | | |
|---|---|---|---|
| 3,259,465 A * | 7/1966 | Sheen | 422/81 |
| 4,653,327 A | 3/1987 | Vartersian | |
| 4,927,299 A * | 5/1990 | Ramalingam et al. | 407/120 |
| 5,014,556 A * | 5/1991 | Dunegan | 73/587 |
| 5,094,108 A * | 3/1992 | Kim et al. | 73/627 |
| 5,119,551 A | 6/1992 | Abbott | |
| 5,191,796 A * | 3/1993 | Kishi et al. | 73/632 |
| 5,329,698 A | 7/1994 | Abbott | |
| 5,980,837 A * | 11/1999 | Umin et al. | 422/179 |
| 6,173,613 B1 * | 1/2001 | Dunegan | 73/587 |
| 6,263,737 B1 * | 7/2001 | Schoess | 73/583 |
| 6,360,608 B1 * | 3/2002 | Dunegan | 73/587 |
| 7,191,656 B2 | 3/2007 | Yagi et al. | |
| 7,900,352 B2 * | 3/2011 | Mayfield | 29/890 |
| 8,182,752 B2 * | 5/2012 | Ten Eyck et al. | 422/179 |
| 2005/0005446 A1 | 1/2005 | Mayfield | |
| 2009/0116533 A1 * | 5/2009 | O'Connell et al. | 374/5 |
| 2010/0039128 A1 | 2/2010 | Nitsch et al. | |

FOREIGN PATENT DOCUMENTS

JP   2005-142495   6/2005

* cited by examiner

*Primary Examiner* — J M Saint Surin
(74) *Attorney, Agent, or Firm* — Harness, Dickey & Pierce, P.L.C.

(57) ABSTRACT

A method of detecting a fracture as it occurs in a component during a manufacturing process includes positioning an acoustic sensor in acoustic communication with the component. A manufacturing process is performed while the acoustic sensor remains in acoustic communication with the component. A signal indicative of acoustic emissions from the component during the manufacturing process is provided to a controller where it is determined whether the component has fractured based on the signal.

17 Claims, 4 Drawing Sheets

ULTRASONIC ACOUSTIC EMISSIONS TO DETECT SUBSTRATE FRACTURE

FIELD

The present disclosure relates to a method of assembling a catalytic converter or other exhaust treatment device. More particularly, a method to detect ultrasonic acoustic emissions from a substrate is discussed.

BACKGROUND

This section provides background information related to the present disclosure which is not necessarily prior art.

Catalytic converters have been useful in motor vehicle exhaust gas systems to convert nitrous oxides, carbon monoxide and/or hydrocarbons to more environmentally friendly compounds. One type of catalytic converter includes one or more ceramic monoliths or substrates mounted inside of a sheet metal housing. The substrates typically contain a multiplicity of longitudinal straight-through-flow exhaust gas passages that are coated with a catalyst.

In many instances, the metal housings used for commercially acceptable converters are formed as "pancake" or "clam shell" designs. These designs include stamped upper and lower shells which are substantially identical to each other. The shells have mating, peripheral side flanges that are welded together along a plane containing the longitudinal axis of the housing. Another commercial form of catalytic housing may be formed from three pieces including a tube with separate end cones welded at each end of the tube.

Other more economically produced catalytic converters may include a singular open-ended metal tube in which the catalyst coated ceramic substrate is inserted. In one method of catalytic converter assembly, the metal tube is radially inwardly compressed around the substrate. In another process, the substrate is pressed into an undersized tube to a fixed position. Regardless of the manufacturing process, care must be taken to avoid damaging the relatively brittle ceramic substrates. Furthermore, substrates that have been cracked or otherwise damaged during assembly are relatively difficult to inspect once the catalytic converter assembly process has been completed and the metal housing substantially precludes access to the substrate. Non-destructive inspection of the completed assembly may not be as reliable as desired. The cost and time associated with post assembly inspection may also be very high. Accordingly, it may be beneficial to provide a non-destructive testing method for detecting substrate fracture during catalytic converter assembly.

SUMMARY

This section provides a general summary of the disclosure, and is not a comprehensive disclosure of its full scope or all of its features.

A method of detecting a fracture as it occurs in a component during a manufacturing process includes positioning an acoustic sensor in acoustic communication with the component. A manufacturing process is performed while the acoustic sensor remains in acoustic communication with the component. A signal indicative of acoustic emissions from the component during the manufacturing process is provided to a controller where it is determined whether the component has fractured based on the signal.

A method of detecting a fracture in a component of an exhaust treatment device as it occurs during a manufacturing process includes positioning an acoustic sensor in acoustic communication with the exhaust treatment device. A manufacturing process is performed on the exhaust treatment device while the acoustic sensor remains in acoustic communication with the exhaust treatment device. A signal from the acoustic sensor is output indicating acoustic emissions from the exhaust treatment device during the manufacturing process. The method includes comparing the signal output by the acoustic sensor to a predetermined value and determining whether the component has fractured based on the comparison.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
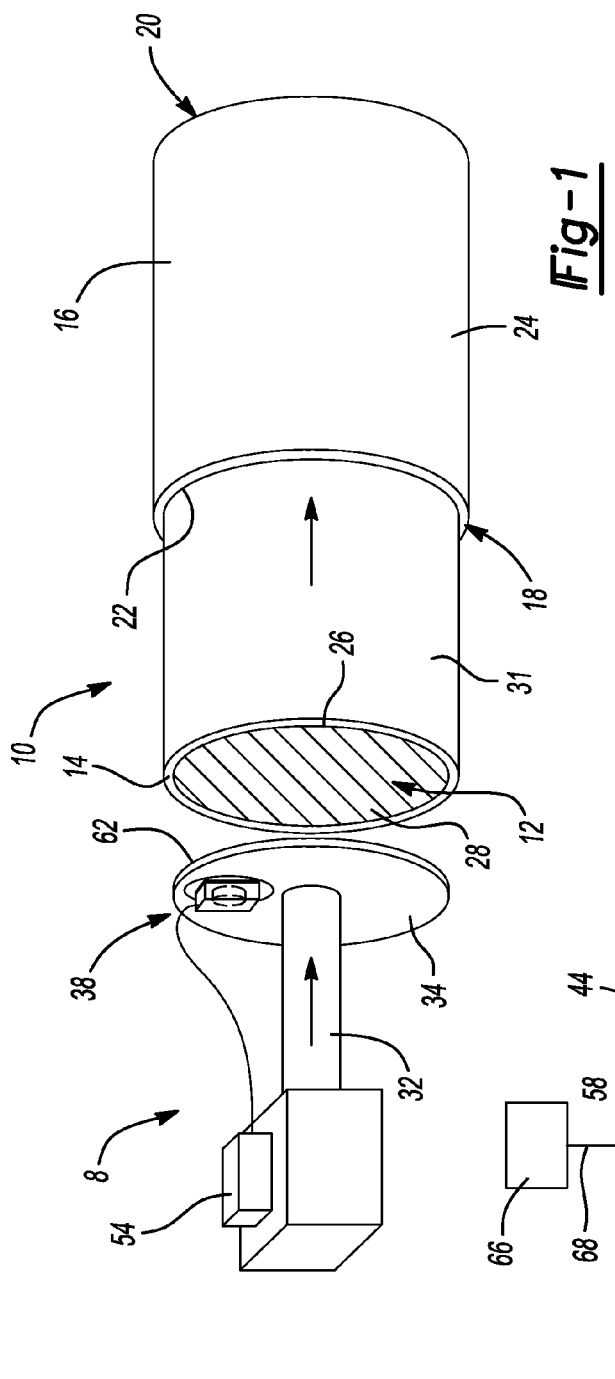
FIG. 1 is a schematic depicting a manufacturing process related to the assembly of an exemplary catalytic converter.

With reference to FIG. 1, a catalytic converter assembly machine is identified at reference numeral 8. Assembly machine 8 is arranged to at least partially assembly an exemplary catalytic converter 10. Catalytic converter 10 includes a ceramic substrate 12 wrapped with a compressible mat 14 and positioned within a tubular housing 16.

Housing 16 is depicted as a hollow right circular cylinder having an open first end 18 and an opposite end 20. Housing 16 includes an inner cylindrical surface 22 and an outer cylindrical surface 24. It should be appreciated that other tubular shapes are also contemplated as being within the scope of the present disclosure. Accordingly, housing 16 may have any number of cross-sectional shapes including elongated slot, elliptical, square, polygonal, or other shape.

Substrate 12 is shaped as a right circular cylinder having an outer cylindrical surface 26 and a first substantially planar end face 28 and an opposite substantially planar end face 30. At the beginning of the assembly process, mat 14 is wrapped around substrate 12 in contact with cylindrical surface 26. Mat 14 functions to support substrate 12 within housing 16 providing thermal and acoustically shielding, as well. It has been determined that mat 14 performs the above functions best when compressed to a predefined thickness. An outer cylindrical surface 31 of mat 14 defines an outer diameter greater than an inner diameter of inner cylindrical surface 22. As such, radial compression of mat 14 is required to assemble catalytic converter 10.

One method of radial compression is combined with axially inserting the mat/substrate combination into housing 16 and includes using a stuffing cone, such as disclosed in U.S. Pat. Nos. 6,532,659 and 6,732,432. With the devices shown in these patents, an outlet of the stuffing cone is disposed adjacent to opening 18 of housing 16. The cone structure has an inner diameter less than the inner diameter of the housing. As the mat and substrate combination moves through the stuffing cone toward the housing, the cone compresses compressible mat 14 about substrate 12 so that the subassembly can be axially translated into housing 16. As the mat and substrate combination slide against the inwardly tapered interior of the stuffing cone, mat 14 compresses about substrate 12 until the combination has an outer diameter less than an inner diameter of inner cylindrical surface 22. At this point, the mat and substrate combination is pushed or stuffed into housing 16. In an alternate process, the mat may be compressed via a fluid bearing as disclosed in published patent application no. US2007/0148057.

During the stuffing operation, substrate 12 may inadvertently contact housing 16. During this contact, a portion, such as an edge, of substrate 12 may be chipped or the substrate may be cracked. The stuffing operation may also cause mat 14 to roll or bunch due to the shear forces generated between mat 14 and housing 16 during the stuffing process. As substrate 12 and mat 14 are further driven into housing 16, stresses may increase to the point of fracturing or otherwise damaging substrate 12.

Figure 2:
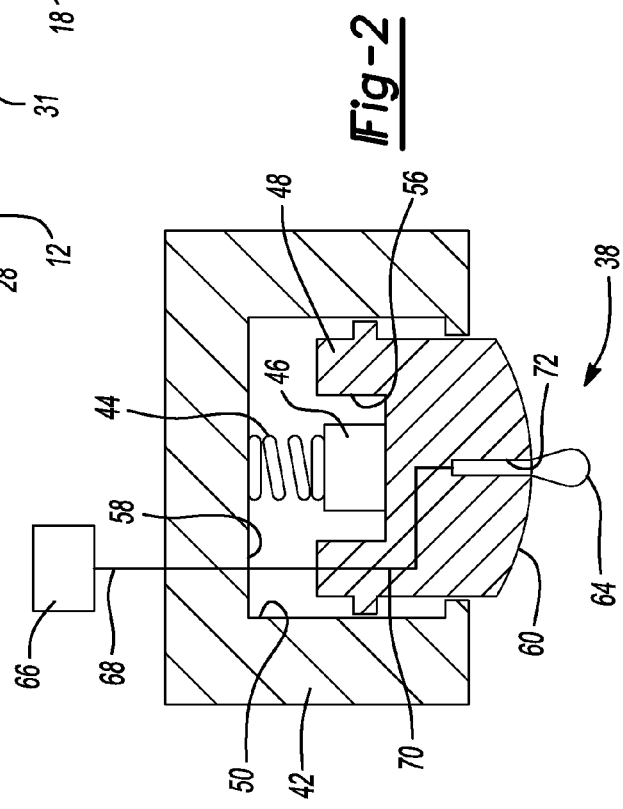
FIG. 2 is a cross-sectional view of an acoustic sensor assembly for detecting fracture of a component during an assembly process.

Assembly machine 8 performs the stuffing operation and includes a ram 32 fixed to a plate 34. Ram 32 is coupled to a hydraulic press and is operable to move along the axis of ram 32. A sensor assembly 38 is coupled to plate 34. Sensor assembly 38 is depicted in FIG. 2 to include a mounting block 42, a spring 44, a sensor 46 and a wave guide 48. Mounting block 42 is preferably constructed from a plastic material such as Delrin® or an ultra high molecular weight material. Mounting block 42 is fixed to plate 34 and includes a pocket 50 in receipt of spring 44, sensor 46 and at least a portion of wave guide 48.

Sensor 46 is an acoustical monitoring device operable to output a signal indicative of the magnitude and frequency of acoustic waves emanating from substrate 12. Sensor 46 is in communication with a controller 54 (FIG. 1) programmed to compare the signal provided by sensor 46 to a predetermined acoustical output and determine whether the substrate has been chipped, cracked or otherwise damaged.

Wave guide 48 serves to protect sensor 46 from possible damage during the assembly process and may be constructed from a metal stamping sized to axially translate within pocket 50. Wave guide 48 includes a recess 56 in receipt of sensor 46. Spring 44 engages a wall 58 of mounting block 42 and biases sensor 46 and wave guide 48 away from mounting block 42. Wave guide 48 includes a convex contact surface 60 that protrudes from a bottom face 62 of plate 34. The amount of axial travel allowed between wave guide 48 and mounting block 42 exceeds the distance that convex surface 60 extends beyond surface 62 of plate 34. In this manner, load provided by ram 32 is transferred through plate 34 to substrate 12 and not through the sensor 46. Sensor 46 and wave guide 48 are only loaded against substrate 12 to the extent that spring 44 allows.

To obtain an accurate acoustic signal, it may be desirable to minimize noise generated during the catalytic converter assembly process. One source of noise may occur when wave guide 48 moves relative to end face 28 of substrate 12. To minimize this noise generation source, the shape of the end of wave guide 48 is curved as previously discussed. Furthermore, a lubricant or an acoustic couplant 64 may be provided between the interface of convex surface 60 and end face 28.

In an automated production process, it may be desirable to automatically dispense couplant 64 to surface 60 prior to engaging wave guide 48 with each substrate 12. Couplant 64 may be stored within a container 66 and pumped or otherwise dispensed through a line 68 and a passageway 70 extending through wave guide 48. Passageway 70 terminates at an outlet 72 positioned at or near the apex of convex surface 60. By arranging sensor assembly 38 relative to plate 34 in the manner described, wave guide 48 will contact substrate 12 prior to the application of insertion force by ram 32. Acoustic monitoring or crack detection may occur during the entire process for which a load is applied to substrate 12. It should be appreciated that the axial load applied by ram 32 may be substantial because further compression of mat 14 may need to occur during the stuffing process.

Figure 3:
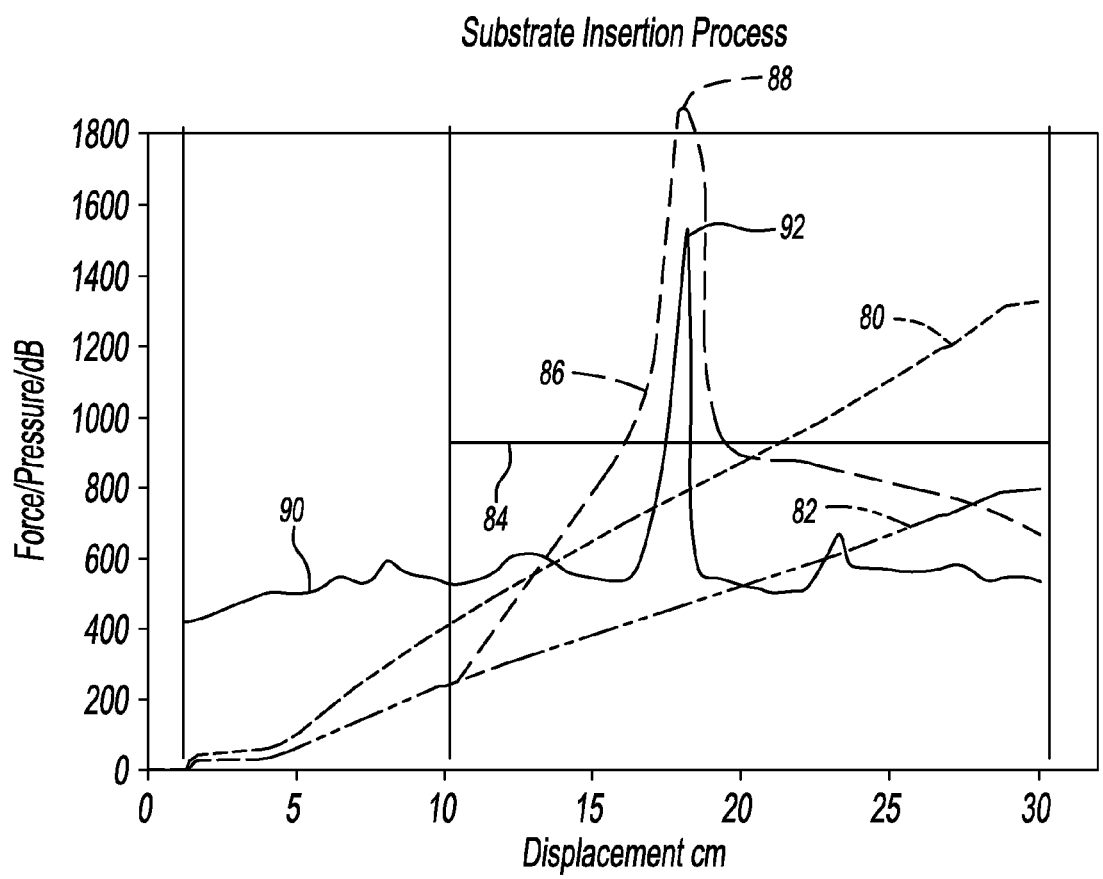
FIG. 3 is a graph depicting component insertion force versus displacement as well as acoustic sensor output for the process performed using the apparatus of FIG. 1.

With reference to FIG. 3, a force versus displacement graph depicting an exemplary stuffing operation overlies a trace of acoustic output versus time representing a crack being formed in the substrate during the stuffing process. More particularly, a first trace 80 depicts the axial force provided by ram 32 during a stuffing operation. This trace may represent the axial force for a "properly installed" substrate and mat. It should be appreciated that a similar curve may result when an undesirable event such as rolling or bunching of mat 14 occurs. Accordingly, it may be desirable to utilize sensor 46 to determine if substrate 12 has been damaged during the stuffing process. FIG. 3 also depicts a trace 82 showing radial pressure acting on mat 14 and substrate 12 during a desired or "normal" stuffing process. The maximum radial pressure remains below a radial pressure limit identified at line 84. A trace 86 represents the radial pressure acting on mat 14 and substrate 12 during assembly of a defective catalytic converter 10. As is shown in the graph, the radial pressure rapidly increases to a peak pressure 88 that is substantially greater than the radial pressure limit 84. At the maximum radial pressure, substrate 12 cracks. The stress is relieved and the radial pressure decreases as the mat 14 and substrate 12 are continued to be stuffed within housing 16.

Another trace 90 of FIG. 3 depicts an exemplary output from sensor 46. A peak magnitude on the acoustic trace occurs at point 92. Point 92 corresponds to the occurrence of a crack in substrate 12. During the cracking event, sound is emitted from substrate 12. Controller 54 may be programmed to output a signal corresponding to point 92 when the magnitude of acoustic emission measured is greater than a predetermined maximum.

Figure 4:
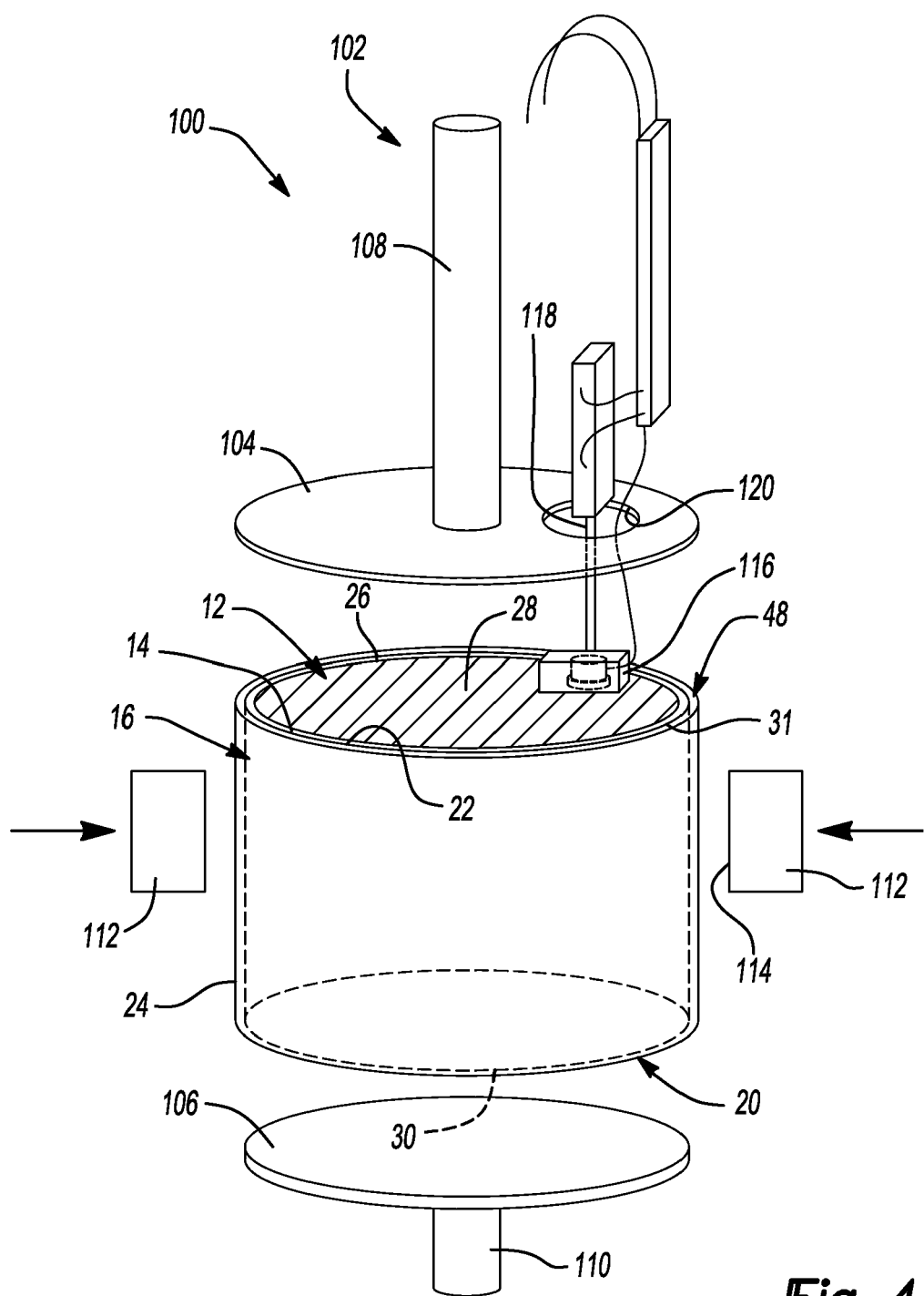
FIG. 4 is a schematic view of another work station for performing a sizing operation on a catalytic converter.

With reference to FIG. 4, another catalytic converter assembly machine is identified at reference numeral 100. Assembly machine 100 is operable to radially inwardly compress housing 16 to further secure substrate 12 therein. Assembly machine 100 is operable to perform a sizing operation subsequent to the stuffing operation performed by assembly machine 8. The sizing operation compresses mat 14 to the target predetermined thickness earlier described. A transfer apparatus 102 includes an upper clamp plate 104 and a lower clamp plate 106 operable to engage and capture tubular housing 16 therebetween. Sufficient load is applied through an upper rod 108 and a lower rod 110 to transfer the subassembly of substrate 12, mat 14 and housing 16 created by assembly machine 8 into communication with radially moveable jaws 112 of assembly machine 100.

Jaws 112 are circumferentially spaced about a perimeter of a cavity 114. The inner diameter of cavity 114 may vary based on the radial position of jaws 112. At an open position, jaws 112 are retracted to a radial outward position thereby defining a maximum inner diameter. At this time, the substrate, mat and housing assembly is positioned within cavity 114 by axially translating rods 108, 110.

A retractable sensor head 116 is configured substantially similarly to sensor assembly 38 previously described. Accordingly, like elements will retain their previously introduced reference numerals. Retractable sensor head 116 is coupled to an axially moveable slide 118. Slide 118 and retractable sensor head 116 pass through an aperture 120 formed in upper clamp plate 104. Wave guide 48 is placed in contact with end face 28 prior to radial inward movement of jaws 112. If desired, slide 118 may be actuated to place wave guide 48 in contact with end face 28 prior to engagement of clamp plates 104, 106 with housing 16.

Once the substrate, mat and housing assembly have been positioned within cavity 114, upper rod 108 and lower rod 110 axially translate away from one another to retract upper clamp plate 104 and lower clamp plate 106 out of communication with jaws 112. Jaws 112 are moved radially inwardly to contact outer cylindrical surface 24 and reduce the outer diameter of housing 16. By moving the cylindrical wall of housing 16 radially inwardly, mat 14 is further compressed. Jaws 112 are controlled to move radially inwardly a desired amount to properly "size" housing 16 and compress mat 14 to the desired thickness. At the end of the sizing operation, jaws 112 are once again radially outwardly moved to maximize the inner diameter of cavity 114. Assembly machine 100 causes upper rod 108 and lower rod 110 to move toward one another and engage upper clamp plate 104 with one end of housing 16 and lower clamp plate 106 with an opposite end of housing 16 to transfer the sized substrate, mat and housing assembly out of cavity 114.

Figure 5:
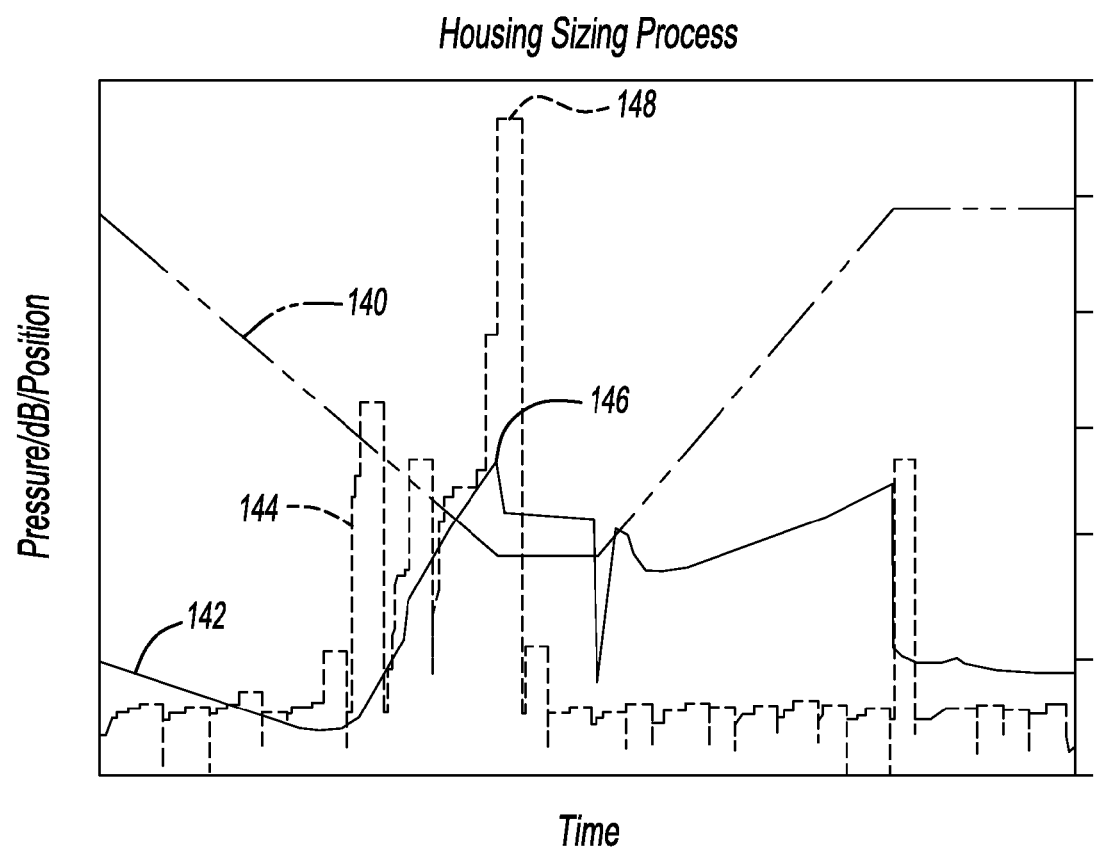
FIG. 5 is a graph depicting machine operating characteristics as well as an acoustic output signal associated with a manufacturing operation using the apparatus of FIG. 4.

FIG. 5 provides a trace 140 indicative of the radial position of jaws 112. A trace 142 represents the radial pressure acting on mat 14 and substrate 12 during the sizing operation. A trace 144 represents the output of acoustic sensor 46 during a sizing operation. As jaws 112 move radially inwardly, as indicated by the downward sloping direction of trace 140, the radial pressure illustrated by trace 142 increases. At or near a point of maximum radial pressure 146, a crack occurs in substrate 12. An acoustic emission emanates from the crack site. Sensor 46 detects the acoustic emission and outputs a maximum acoustic sensor signal output at a point 148. Controller 54 determines whether the maximum detected magnitude of trace 144 exceeds a predetermined acceptable maximum. A fault signal is output when the actual magnitude exceeds the predetermined maximum value.

From the above description, it should be appreciated that the present disclosure relates to crack detection and acoustic monitoring in a production assembly environment. It is contemplated that a number of acoustic sensor assemblies 38 may be positioned throughout the assembly process to collect acoustical data and detect cracks at one or more assembly stages. Furthermore, it is contemplated that additional acoustic sensor assemblies 38 may be positioned to contact substrate 12 before and during each transfer and/or handling step. In this manner, real time crack detection may be performed to greatly minimize and possibly eliminate the need for after-assembly catalytic converter inspection. At a minimum, it is contemplated that the assembly machines and processes described herein may be useful for identifying individual ceramic substrates that may require off-line inspection after the assembly processes have been completed.

If further detail is required regarding crack initiation, three or more sensor assemblies 38 may be positioned in contact with a single substrate 12. Controller 54 may be operable to compare the output of each sensor assembly 38 on a real-time basis in order to perform a triangulation method to locate the substrate crack in 3D space. Furthermore, while sensor assembly 38 has been shown for use in communication with ceramic substrate 12, it is contemplated that acoustic detection for the handling and assembly of other components may be implemented as well.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of detecting a fracture as it occurs in a component during a manufacturing process, the method comprising:
    positioning an acoustic sensor in acoustic communication with the component;
    performing a manufacturing process while the acoustic sensor remains in acoustic communication with the component;
    providing a signal indicative of acoustic emissions from the component during the manufacturing process to a controller; and
    determining whether the component has fractured by comparing the magnitude of the signal to a predetermined maximum.

2. The method of claim 1 further including biasedly engaging the acoustic sensor with the component.

3. The method of claim 2 further including positioning a transducer in contact with a metallic wave guide to define the acoustic sensor.

4. The method of claim 3 further including providing the wave guide with a convex surface and engaging the convex surface with the component.

5. The method of claim 4 further including automatically dispensing an acoustic couplant at the interface of the wave guide and the component.

6. The method of claim 1 further including indicating that a fracture has occurred when the signal magnitude exceeds the predetermined maximum.

7. The method of claim 1 wherein the manufacturing process includes inserting a catalytic converter substrate into a housing.

8. The method of claim 7 further including reducing an outer diameter of the housing while providing the acoustic emissions signal.

9. The method of claim 7 wherein the acoustic sensor is positioned in contact with the substrate.

10. The method of claim 9 wherein the substrate includes a ceramic material.

11. A method of detecting a fracture in a component of an exhaust treatment device as it occurs during a manufacturing process, the method comprising:
    positioning an acoustic sensor in acoustic communication with the exhaust treatment device;

performing a manufacturing process on the exhaust treatment device while the acoustic sensor remains in acoustic communication with the exhaust treatment device;
outputting a signal from the acoustic sensor indicative of acoustic emissions from the exhaust treatment device during the manufacturing process;
comparing the signal to a predetermined value; and
determining whether the exhaust treatment device has fractured based on the comparison.

12. The method of claim 11 further including biasedly engaging the acoustic sensor with the exhaust treatment device.

13. The method of claim 12 wherein the sensor is biasedly engaged with the exhaust treatment device prior to initiation of the manufacturing process.

14. The method of claim 11 wherein the manufacturing process includes axially translating a ceramic substrate into a housing.

15. The method of claim 11 wherein the manufacturing process includes radially reducing the size of the housing.

16. The method of claim 11 wherein the manufacturing process includes transporting a component of the exhaust treatment device between manufacturing work stations.

17. The method of claim 11 further including mounting the acoustic sensor to a slide and moving the sensor relative to the exhaust treatment device independent of a clamping device acting on the exhaust treatment device.

* * * * *